(12) United States Patent
Zhu et al.

(10) Patent No.: US 8,295,430 B2
(45) Date of Patent: Oct. 23, 2012

(54) IMAGE GUIDED RADIATION THERAPY

(75) Inventors: Haoqin Zhu, Winnipeg (CA); Labros Petropoulos, Chagrin Falls, OH (US); Alexander Shvartsberg, Winnipeg (CA)

(73) Assignee: Imris Inc., Winnipeg, MB (CA)

( * ) Notice: Subject to any disclaimer, the term of this patent is extended or adjusted under 35 U.S.C. 154(b) by 352 days.

(21) Appl. No.: 12/792,383

(22) Filed: Jun. 2, 2010

(65) Prior Publication Data
US 2010/0329414 A1  Dec. 30, 2010

Related U.S. Application Data

(60) Provisional application No. 61/221,267, filed on Jun. 29, 2009.

(51) Int. Cl.
*A61B 6/00* (2006.01)
*A61N 5/10* (2006.01)

(52) U.S. Cl. ................................ 378/4; 378/65
(58) Field of Classification Search ................ 378/4, 62, 378/65, 208; 600/411; 324/318, 309
See application file for complete search history.

(56) References Cited

U.S. PATENT DOCUMENTS

| 5,370,117 A | 12/1994 | McLaurin, Jr. |
| 5,947,981 A | 9/1999 | Cosman |
| 7,073,508 B2 | 7/2006 | Moyers |
| 2004/0165696 A1* | 8/2004 | Lee .................................. 378/65 |
| 2009/0149735 A1* | 6/2009 | Fallone et al. ................ 600/411 |

FOREIGN PATENT DOCUMENTS
WO  WO2006083703  8/2006
* cited by examiner

*Primary Examiner* — Irakli Kiknadze
(74) *Attorney, Agent, or Firm* — Adrian D. Battison; Ade & Company Inc.

(57) ABSTRACT

Radiation therapy of a lesion in a part of a patient is carried out by maintaining the patient on a patient support table in fixed position using an immobilization device while the table is rotated between a magnetic resonance imaging system, a CT imaging system for generating a 360 degree scanned image of the patient at the location of the lesion and the radiation therapy system for generating a beam of radiation for treatment of the lesion and for scanning the beam 360 degrees around the lesion. The MR image locates the lesion and the CT system is used to calculate the treatment. Registration between the MR image, the CT image and the radiation treatment is provided by the fixed position of the part of the patient on the table which is held fixed using an immobilization system suitable for the part concerned which may include a molded head mask where the head is involved.

16 Claims, 8 Drawing Sheets

IMAGE GUIDED RADIATION THERAPY

This application claims the benefit under 35 U.S.C. 119 of Provisional Application Ser. No. 61/221,267 filed Jun. 29, 2009.

This invention relates to a system for use in radiation therapy of a lesion in a part of a patient.

BACKGROUND OF THE INVENTION

LINAC radiation therapy systems are well known and widely used for radiation treatment of lesions at various locations in the body of the patient. The LINAC device rotates around the body part and applies a variable intensity of radiation to radiate the lesion as accurately as possible.

Typically it is known that an initial CT scan is carried out to plan the treatment using the attenuation data available from the CT image. The CT imaging is effected at a separate location and it is necessary to register the image of the CT scan with the treatment device to use the attenuation data. For this purpose a head-neck extension board is located on the LINAC's table and on the CT table with the same locking space. Also the patient's head is located on the head neck extension board by a mouldable thermoplastic mask. This is intended to ensure that the patient is located in the same location as the patient moves from the CT image system to the LINAC treatment system.

Thus the head-neck mask is the common reference frame between the two devices. Moreover, CT compatible fiducials are provided on the head-neck mask.

A coned beam CT (CBCT) that is integrated with LINAC's structural frame and has the same point of rotation as the LINAC is used to correlate 3D low resolution CT images from the CBCT with the ones obtained from the CT imaging system and utilized for the planning phase. If the correlation of the bony areas of the patient near the area of treatment coincide, then the planning treatment with the LINAC can proceed. The common point between the CBCT, the regular CT scanner is head-neck mask that conforms to the exact shape of the head and neck by inserting the mask into a hot water solution and then place it firmly over the head and neck region. This conformance the mask is unique to every individual treated and accompanies the individual to every stage of the radiation therapy form the acquisition of the CT image, to the planning stage to the treatment with LINAC.

The center point of interest on the CT scanner is determined by a set of 3 laser beams that are aligned with the three fiducials on the mask and coincide at a point which is the same rotational point used on the CBCT and LINAC set. Thus by identifying this point it is able to superimpose the images from CBCT, to previously collected images from CT and ensure that the patient is positioned correctly for the LINAC treatment.

This system is widely used and has been found to have a relatively low accuracy which can often be as poor as 2 cms so that the treatment has to follow a very conservative course to avoid radiation to healthy tissue. Thus a higher number of treatments with a lower dose of radiation is typically necessary than would theoretically be necessary.

It is also appreciated that MR imaging provides a much more suitable image of the lesion. For this reason one development in this area is to provide a combination of an MR imaging system with a LINAC so that the patient can remain in the MR imaging system location when the LINAC treatment is carried out. Philips Medical Systems (see attached paper).

With MRI, a high field magnet, typically superconducting, is arranged in a torus configuration and with the patient lying down inside the magnet on a table where the magnetic field allows a pulsed and sequenced magnetic and EM field to probe the body to produce images, which allow the trained radiologist to determine with high probability the anatomy of the patient. MRI techniques are very good at detecting the anatomical location of different diseases, for example, tumours.

The magnet for highest field strength is generally cylindrical with the patient lying along the bore but other magnet shapes and arrangements are used in lower strength configurations.

Most MR imaging is carried out on a diagnostic basis where the patient is placed on a diagnostic table which moves into the bore and carries the patient to a required position. In these cases the patient is normally conscious and thus can be moved to the required location on the table so that, when the table enters the bore, the part of the patient to be imaged is located relative to the table so that it enters the bore at the field of view of the MR system, generally at the center of the bore on the axis. In most cases therefore the table is movable only longitudinally of the bore to move the patient into and out of the bore.

The table also is prevented from any significant movement relative to the bore since it includes mechanical structures which fill the available part cylindrical area underneath the surface of the table.

In U.S. Pat. No. 5,735,278 (Hoult et al) issued Apr. 7, 1998, disclosed a medical procedure where a magnet is movable longitudinally relative to the table and to the patient on the table. The moving magnet system allows intra-operative MRI imaging to occur more easily in neurosurgery patients, and has additional applications for liver, breast, spine and cardiac surgery patients. The table is set up for the required surgery and the magnet is moved into place over the table to effect the imaging. The table can tilt about a transverse axis and rotate about a longitudinal axis.

Related disclosures are made in U.S. application Ser. Nos. 12/333,032 filed Dec. 11, 2008 (Publication 20090306495 Dec. 10, 2009) and 12/420,859 filed Apr. 8, 2009 (Publication 2009/0306494 Dec. 10, 2009) by the present Assignees, the disclosures of which are incorporated herein by reference, which correspond to PCT Applications CA/2009/000672 and CA/2009/00673 filed May 25, 2009, to which reference may be made for further detail.

U.S. Pat. No. 7,319,325 (Petot) issued Jan. 15, 2008 and assigned to Philips claims the use of a position sensor to provide feed back to the drive system of a table within the bore of an MRI magnet. The movement as disclosed appears to be simply linear movement along the bore.

U.S. Pat. No. 7,486,076 (Nagao) issued Feb. 3, 2009 and assigned to Ricoh or Hitachi discloses moving the table based on information relating to the difference between the actual position and a desired position. Movement in a second direction at right angles to the longitudinal direction is possible during whole body scanning.

U.S. Pat. No. 6,822,447 (Yamagata) issued Nov. 23, 2004 and assigned to Toshiba discloses moving the table in two directions to move the point of interest to the required imaging position in the magnet.

U.S. Pat. No. 6,045,262 (Igeta) issued Apr. 4, 2000 and assigned to Hitachi discloses a table which is used in X-ray and MRI which can be moved in two directions.

Published US Patent Application 2005/0154291 (Zhao) published Jul. 14, 2005 discloses a table which is used in MRI which can be moved in two directions and tilted during imaging in the magnet.

SUMMARY OF THE INVENTION

It is one object of the invention to provide an improved method and apparatus for radiation treatment which allows an increased accuracy with the possibility of higher doses and lower numbers of treatments while avoiding damaging healthy tissue.

According to one aspect of the invention there is provided a system for use in radiation therapy of a lesion in a part of a patient comprising:

a patient support table for receiving and supporting the patient during planning for and effecting of the therapy of the lesion;

an immobilization device for locating the part of the patient on the table so as to remain fixed relative to the table during the planning and therapy;

a magnetic resonance imaging system for obtaining MR images of the lesion of the patient including a magnet, at least one RF coil and an imaging control system;

a CT imaging system for generating a 360 degree scanned image of the patient at the location of the lesion;

a radiation therapy system for generating a beam of radiation for treatment of the lesion and for scanning the beam 360 degrees around the lesion;

the magnetic resonance imaging system, CT imaging system and the radiation therapy system being arranged at angularly spaced positions around the patient support table the magnetic resonance imaging system being arranged so as to provide relative movement between the table and the system to enable the imaging of the patient while the patient remains in fixed position on the table;

the CT imaging system being arranged so as to provide relative movement between the table and the system to enable the imaging of the patient while the patient remains in fixed position on the table;

the radiation therapy system being arranged so as to provide relative movement between the table and the system to enable the radiation treatment of the patient while the patient remains in fixed position on the table;

the CT imaging system and the radiation therapy system being arranged so that the image and the treatment being arranged such that they lie in a common plane around the lesion in the patient;

the table and immobilization device being MR compatible, radiation translucent, and non-conductive so as to allow the imaging and treatment of the patient while stationary on the table;

and a treatment control system arranged to locate the lesion using the MR image and to plan the radiation treatment to vary the intensity of radiation around the plane using the CT image.

Preferably the immobilization device includes a head neck thermoplastic mask which is molded to match the patient anatomy.

Preferably the immobilization device includes an immobilization board arranged to be placed in fixed position on the table.

Preferably the RF coil includes a base part which is incorporated into the immobilization board which is capable of accepting the head neck thermoplastic mask.

Other immobilization devices can also be tailored for other body parts such as for the abdomen, pelvis, upper extremities and lower extremities.

Preferably the table includes a perforated section located underneath the location of the lesion.

Preferably the perforated section is located at a perforated head extension board.

Preferably the head extension board is formed of a fiber reinforced resin material where the fibers are non-conductive.

Preferably the table rotates around a vertical axis through the table so as to line up the table with the magnet, the CT scanning system and the radiation therapy system.

Preferably the table is movable to the respective positions only by rotation around the axis. However some lateral or translational movement my be provided by a suitable mounting linkage arrangement.

Preferably the magnet is movable longitudinally so as to move into cooperation with the table.

Preferably the CT scanning system is movable relative to the table.

Preferably the radiation treatment system is movable relative to the table.

Preferably wherein the RF coil includes an anterior coil which is flexible so as to drape over the part of the patient.

Preferably registration between the MR image, the CT image and the radiation treatment is provided by the fixed position of the part of the patient on the table.

Preferably the RF coil includes a flexible or semi flexible neck piece that conforms to all the variety of neck sizes and extends up the lower torso area.

Preferably the immobilization board is made from Kevlar composite with conjunction of the urethane or Rohacell (trade mark) foams that is both radiolucent and MR compatible and has a cavity that incorporates the lower head portion of the head array coil that can be removable during radiation therapy procedure.

Preferably the patient support table is arranged for movements which include at least:

longitudinal movement along the longitudinal axis of the table transverse movement side to side;

rolling movement about a longitudinal axis of the table;

tilting movement about a transverse axis of the table;

a bending movement of the table relative to a transverse hinge line in the table at a position spaced from the ends of the table;

the control system being arranged to effect said movements while the patient support table is within the field of view.

Preferably the table includes a pedestal base, a table member mounted on the pedestal base and a replaceable table top portion which is mounted on the table member.

Preferably the pedestal base and table member are movable to provide said longitudinal movement along the longitudinal axis of the table, said transverse movement side to side, said rolling movement about a longitudinal axis of the table and said tilting movement about a transverse axis of the table.

Preferably the replaceable table top portion includes said bending movement of the table relative to a transverse hinge line in the table top portion at a position spaced from the ends of the table.

Preferably the pedestal base can swivel around a vertical axis.

Preferably the table movements include up and down movement.

Preferably the table movements include rotation around a vertical axis.

Preferably the bending movement of the table is both upward and downward of a planar central position of the table.

The movements may include bending movements of the table relative to two or more transverse hinge lines in the table.

Preferably the table is arranged to receive the patient lying on the table and wherein the table includes a first transverse hinge line in the table is at one end of the table at one end of the patient and a second transverse hinge line at a position part way along the patient.

Preferably the table comprises a planar board with a flat top surface and a flat bottom surface generally parallel to the top surface.

Preferably the table has a vertical thickness between the surfaces of less than 2.5 inches.

Preferably wherein the table has pedestal and a table top with the table top cantilevered by a length such that the whole of the patient is carried on the cantilevered portion.

Preferably the pedestal is on wheels for movement of the table. Preferably the movement can be locked.

Preferably the magnet is annular with a horizontal cylindrical bore.

Preferably there is provided an impact detection system for detecting impact of the patient or the table with an interior surface of the bore of the magnet.

In one arrangement, the impact detection system operates by providing a laser transmitter generating a beam and a receiver for the beam and where breaking of the beam is indicative of a potential impact.

In another arrangement, the impact detection system operates by providing a contact sensitive sensing system on the interior surface of the magnet.

In another arrangement, the impact detection system operates by providing a contact sensitive sensing system on the table top.

Preferably the movement is effected by motors which are MR compatible and at least some of which are in the bore during the movement.

In one arrangement, the movement is effected by motors which are electrical.

In another arrangement, the movement is effected by motors which are hydraulic.

Preferably the control system includes an input for entering into a memory a set position of the table and wherein the control system is arranged to return the position of the table to the set position when instructed to do so.

Preferably the control system is arranged to hold the table stationary during imaging.

According to a second aspect of the invention there is provided a method for radiation therapy of a lesion in a part of a patient comprising:

locating the patient on a patient support table for receiving and supporting the patient;

immobilizing the part of the patient on the table;

while the patient remains immobilized on the table, imaging the part of the patient using a magnetic resonance imaging system to obtain MR images of the lesion of the patient to locate the lesion;

while the patient remains immobilized on the table, obtaining a 360 degree CT scanned image of the patient at the location of the lesion;

while the patient remains immobilized on the table, using the 360 degree CT scanned image and the MR image to plan the radiation treatment;

while the patient remains immobilized on the table, applying a beam of radiation for treatment of the lesion and scanning the beam 360 degrees around the lesion at varying intensities so as to follow the planned treatment.

MR is a modality which can provide unprecedented soft tissue contrast far superior than any CT scanner can provide especially in the head and neck area and a true 3D structure of the tumor area. However, for a radiation planning and treatment, CT is required since the calculation of a dose, that is the variation in the intensity around the 360 degree scan base on the variable attenuation, is based on the CT image. This dose calculation is transferred to a planning tool and the projected treatment area is then transferred to a LINAC ration therapy system for the treatment. On the CT scanner area there exists a head extension board that is made from carbon fiber, a material acceptable to CT and LINAC due to low radiolucent levels, but not acceptable to MR due to conductivity issues and concerns of RF heating, on which the head-neck mask is locked on at seven points. Unfortunately the use of the MR images to correlate or fuse with the CT images in order to enhance the tumor identification during the planning stage is done only on the informative level, since there is no way at present to correlate the head-neck board, and the head-neck mask with the ones used from the CT scanner, due to incompatibility of the materials used for the head-neck board. The materials (carbon fiber) are chosen to provide low signature high radio translucency factor for the CT and LINAC machines but are totally incompatible with the MR scanner during the severe safety concerns (RF heating due to the conductive properties of the carbon fiber).

It is necessary to provide RF coils to be used in conjunction with the head-neck mask which match the specific size requirements of the mask.

It is necessary to provide an MR compatible head-neck board to be used for the MR system. Typically in the prior art, the registration of the head-neck mask to the MR images is only superficial and not realistic due of the fact that there is no reference frame to link these two devices.

A new RF coil design is described hereinafter that incorporates the head-neck board using MR compatible material. Although the present invention refers to an array of coils distributed over the head and neck area, the coil arrangement can include quadrature drive transmit/receive coils or an array of transmit receive coils. Although this invention discusses the art of a head-neck RF coil configuration, in a similar manner can be consider a RF coil configuration attached to an abdominal restraining board with the appropriate body retaining thermoplastic solution as well as the pelvis and or the lower extremities.

The arrangement described herein provides a phased array configuration for the head and neck region, where the base part of the coil is incorporated with a MR compatible head-neck board capable of accepting the head-neck thermoplastic mask. A flexible upper array of coils conforming to broad variety of head sizes and a flexible or semi flexible neck piece that conforms to all the variety of neck sizes and extends up the lower torso area.

The arrangement described herein provides a head-neck board made from Kevlar composite with conjunction of the urethane or Rohacell (trade mark) foams available from Evonik Röhm GmbH Kirschenallee 64293 Darmstadt Germany that is both radiolucent and MR compatible and has a cavity that incorporates the lower head portion of the head array coil that can be removable during radiation therapy procedure. A flexible upper array of coils conforming to broad variety of head sizes and a flexible or semi flexible neck piece that conforms to all the variety of neck sizes and extends up the lower torso area.

BRIEF DESCRIPTION OF THE DRAWINGS

One embodiment of the invention will now be described in conjunction with the accompanying drawings in which.

In the drawings like characters of reference indicate corresponding parts in the different figures.

DETAILED DESCRIPTION

Figure 1:
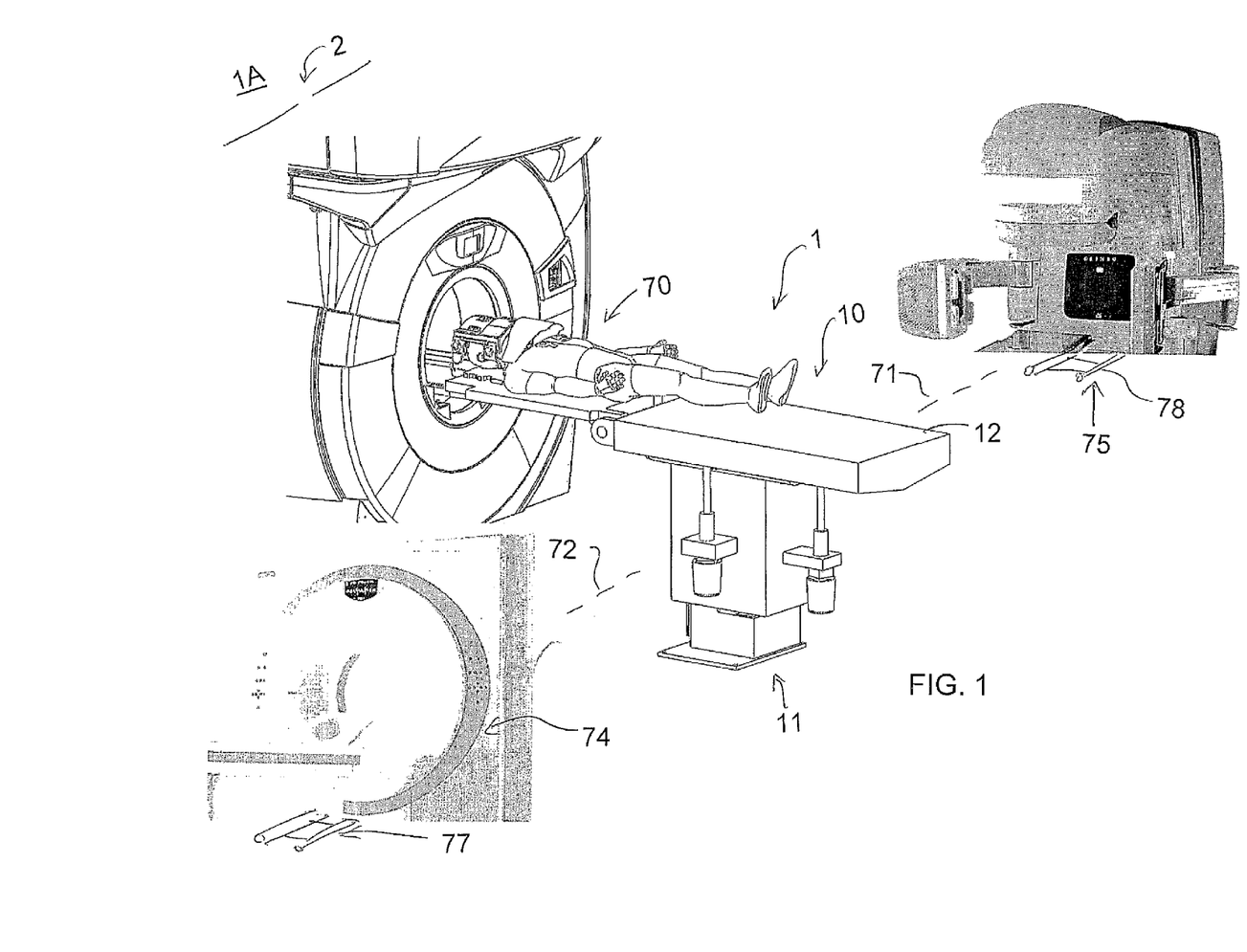
FIG. 1 is an isometric schematic view of one embodiment of a radiation therapy system according to the present invention.

In FIG. 1 is shown an arrangement for carrying out Magnetic Resonance Imaging of a patient while the patient remains stationary on a patient support table. The arrangement provides a room 1 in which is mounted a patient support table 10 with doors 2 at one side of the room for entry into the room of the magnet 3 of an MR imaging system from a magnet bay 1A.

The MR imaging system is a high-field (e.g. 1.5 T or 3 T) magnet that moves on overhead rails between the two or more rooms.

The Patient Handling System or support table is shown in FIG. 1 is indicated generally at 10. The patient support table includes a base or pedestal 11 which allows the base to move a patient support portion 12 to required locations in height and in orientation. At the top of the base 11 is mounted the patient support portion 12 in the form of a generally planar body 12A formed of a fiber reinforced plastics material so as to define a surface area sufficient for supporting the patient while lying on the patient support portion.

Figure 4:
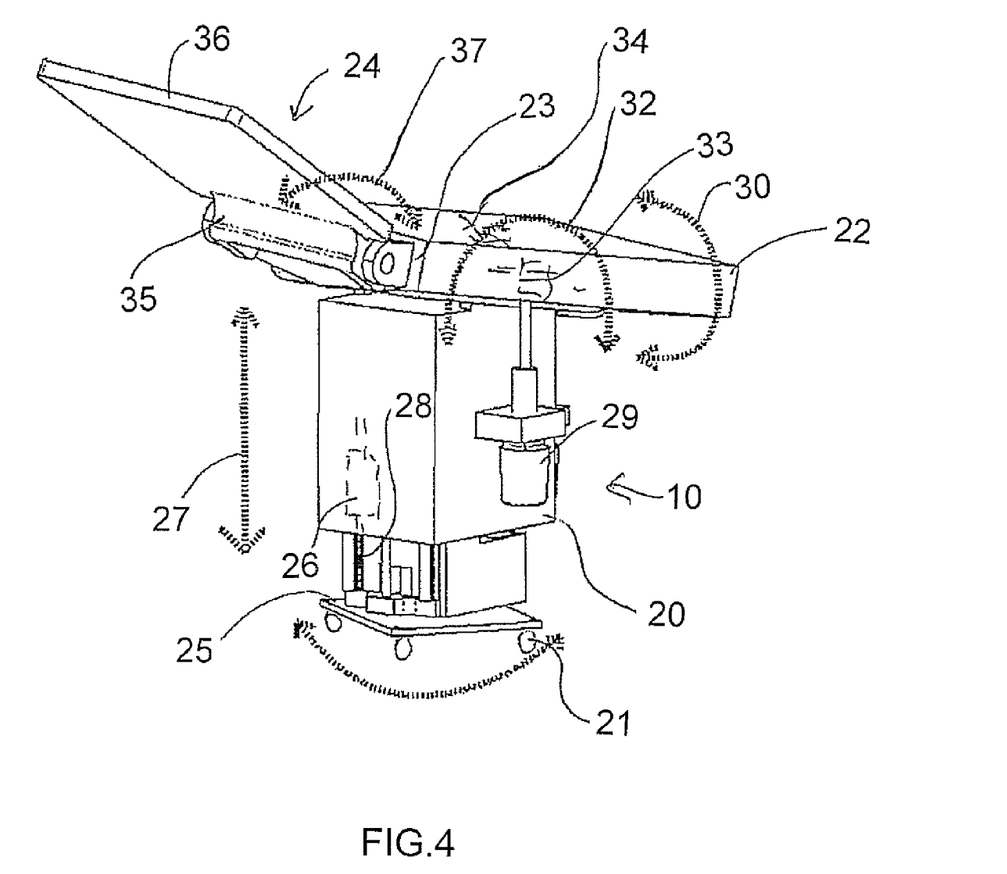
FIG. 4 is an isometric view of the table only of FIG. 1.

In FIG. 4 is shown the table itself which is separate from the magnet 3 of FIG. 1 and is arranged for insertion into one end of the cylindrical bore of the magnet 3 generally at the end of the bore opposite to the conventional diagnostic table 3A of the magnet.

The table 10 comprises a pedestal 20 which can be mounted on ground wheels 21 or the ground wheels may be omitted for increased stability. The ground wheels if present can be locked to prevent transverse movement or can be retracted to place the pedestal base firmly on the floor.

The pedestal base carries at its upper end a table member 22 which is in the form of a generally flat table portion defining a first part of the table on which the patient can lie. The table member includes, at its outer or forward end, a coupling 23 to which a table top portion 24 can be mounted. The coupling 23 provides physical connection from the table top portion 24 to the table member 22 so that forces from the patient lying on the table top portion can be transferred into the table member to hold the patient in fixed position. The table top portion is cantilevered outwardly from the forward end of the table member 22. The table top portion 24 is removable from the coupling 23 so that it is replaceable by alternative constructions for example of the type described hereinafter.

The table member 22 is mounted on the pedestal in a manner which provides movement of the table top member 22 relative to the pedestal in a plurality of different directions.

In a first direction of movement, the pedestal 20 can pivot around a vertical axis relative to a base portion 25 so that the whole of the table can swivel about the vertical axis. Typically this swivel movement is effected manually since it is relatively course movement and since there is sufficient mechanical advantage from the structure of the table to allow easy manual movement of the rotation of the table about the vertical axis.

In addition the pedestal includes a first motor 26 in the form of a linear actuator which can drive upward and downward movement 27 of the pedestal relative to the base. The linear actuator can be of the type including a lead screw shown schematically at 28.

A further motor 29 provides tilting movement of the table member in a rolling action as indicated at 30 around a horizontal axis generally longitudinal of the table.

Figure 2:
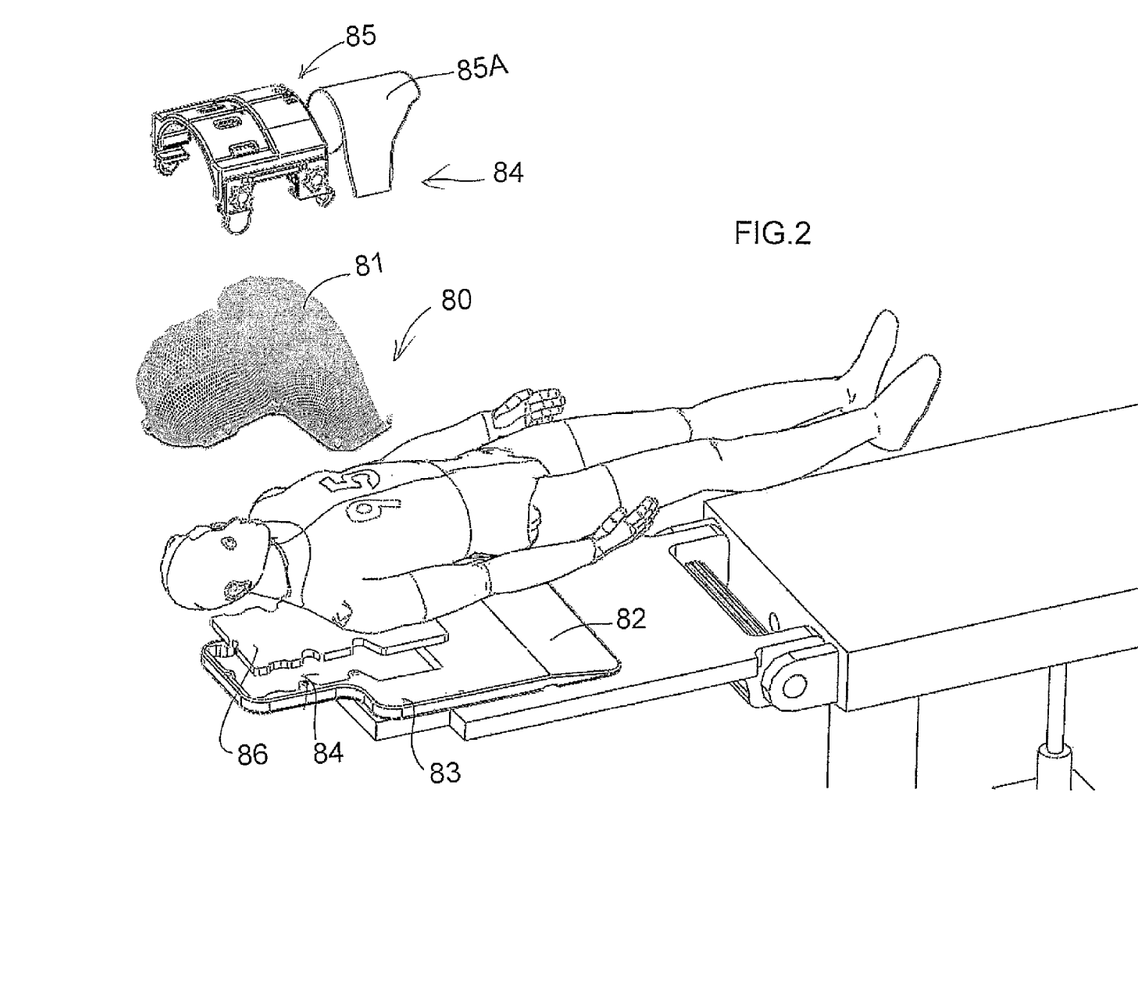
FIG. 2 is an isometric view of one embodiment of the table of FIG. 1 where the components which locate the patient have been exploded for further detail.
Figure 3:
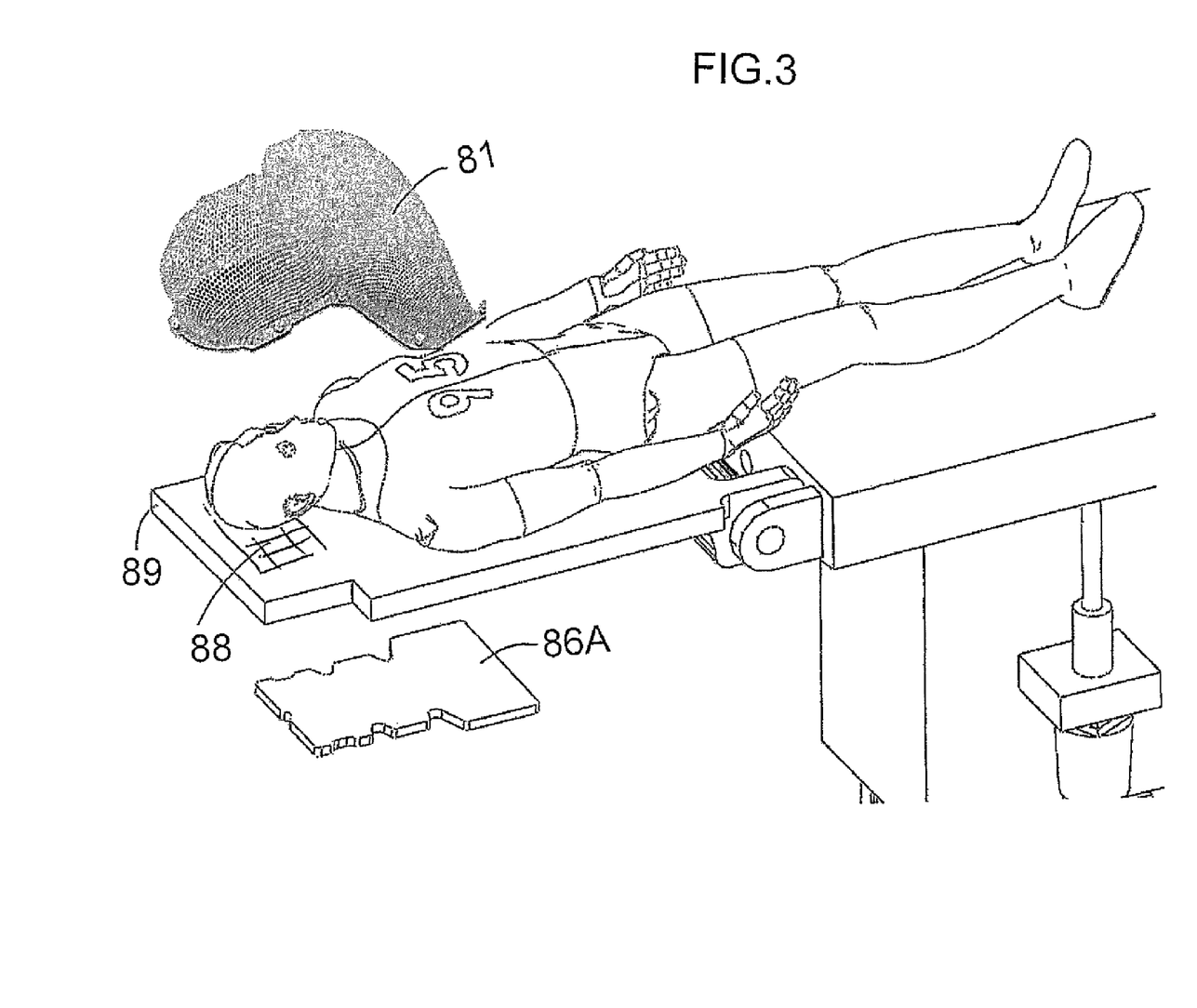
FIG. 3 is an isometric view of a second embodiment of the table of FIG. 1 where the components which locate the patient have been exploded for further detail.

A further motor 31 visible in FIG. 3 provides tilting movement of the table about a transverse axis so as to raise and lower the front end of the table relative to the pedestal and thus tilt the patient about the transverse axis. The tilting movement is shown in FIG. 2 at 32.

Two additional motors are provided as indicated schematically at 33 and 34 which act to provide longitudinal movement of the table forwardly and rearwardly relative to the pedestal and also side to side movement of the table relative to the pedestal.

All four of the above motors are accurate motors providing controlled slow movement of the table top relative to the pedestal so as to ensure accurate positioning of the patient on the table as required.

Figure 7:
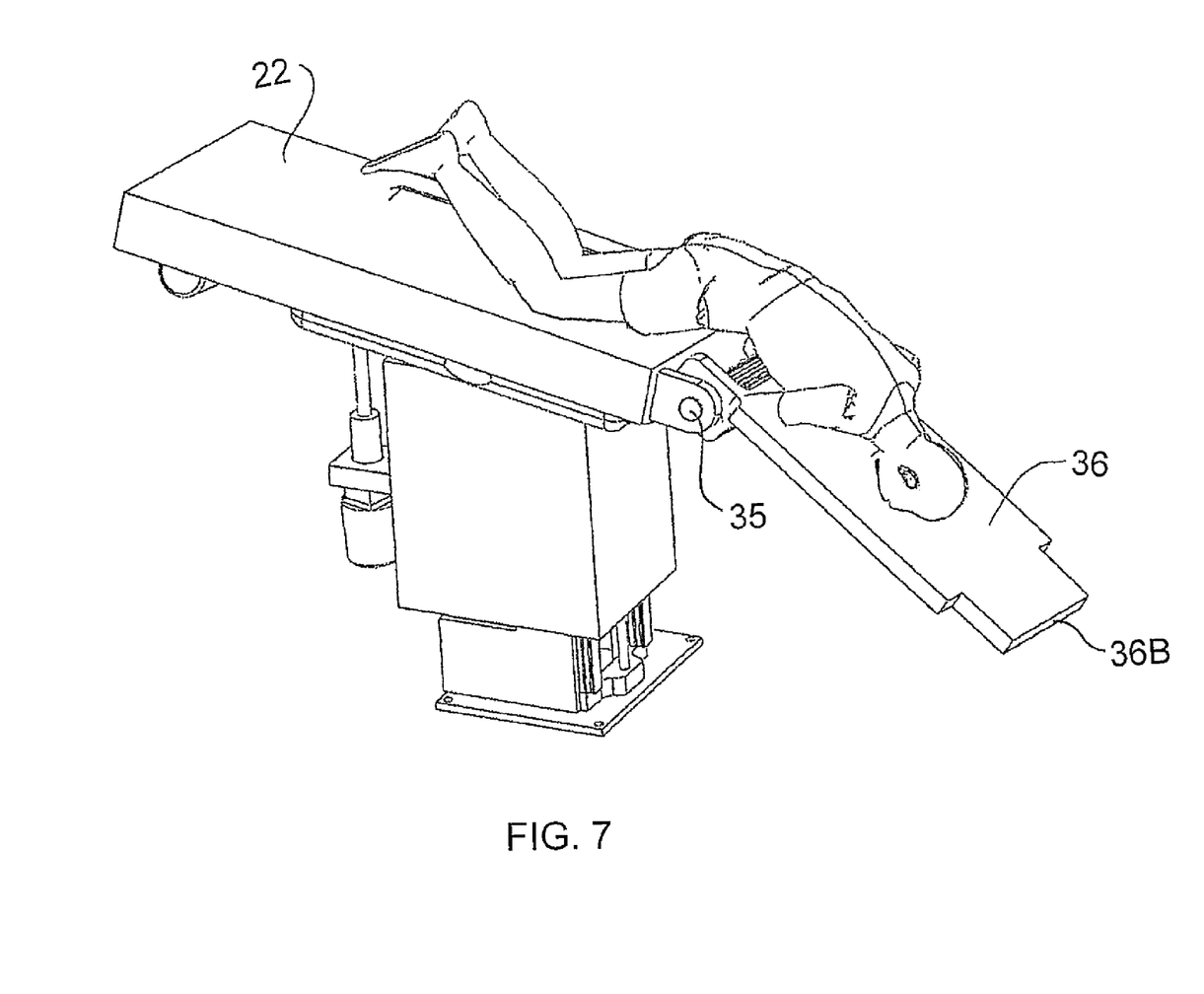
FIG. 7 is an isometric view of the table of FIG. 1 for mounting the patient showing a configuration for spine procedure.

The replaceable table top portion 24 in FIG. 2 includes a transverse hinge 35 which allows a cantilevered portion 36 of the table top portion to be moved upwardly and downwardly to take up different angles as indicated at 37 relative to the main table member 22. This forward portion 36 which is cantilevered beyond the hinge line can pivot upwardly and downwardly to positive and negative angles. As shown in FIG. 3, the portion 36 is pivoted upwardly relative to the table top member 22 so as to provide an angle less than 180°. In FIG. 7, the same table top portion 36 is pivoted downwardly relative to the table member 22.

Alternative arrangements (not shown) can be provided which provide a further transverse hinge line spaced outwardly from the hinge line 35 allowing further bending movement of the table top portion.

In use, the patient is placed upon the table top in a configuration arranged for surgery of the patient at the required location. Further details described hereinafter provide a number of examples of such configurations. However other configurations are also possible.

Thus the patient on the operating table is located in a position which is particularly suitable for operation by the surgeon on the part of the patient to be treated. The surgery does not need to be invasive and any form of intervention is possible using the table structure described. In addition the table structure can be used for radiation treatment where the patient is located in a suitable configuration for the radiation to be applied to the required location.

With the patient arranged for the surgery or other intervention, the patient while remaining in that configuration and while held in that configuration by suitable restraints, can be moved into the bore of the magnet typically by movement of the magnet longitudinally along its length in accordance with the Hoult patent set forth above. Thus the cylindrical bore of the magnet is moved over the table and over the patient on the table with the table adjusted to a position which will allow the magnet to pass over the table and the patient. Thus prior to movement of the magnet, while the patient remains in the configuration required for surgery, the table may be adjusted in height for an angle in accordance with any of the above allowable movements to position the table so that the magnet bore can move over the patient and the table.

In addition, with the magnet in place, the part of the patient is located generally at the field of view within the magnet for imaging.

However the configuration of the patient on the table and the position of the table allowing the movement of the magnet to the required imaging position likely will not position the part of the patient at the best location within the field of view to obtain the desirable imaging parameters.

Thus while the patient and the table are within the bore, the table is adjustable so as to move the part of the patient to the best position for imaging. This movement can be calculated, bearing in mind all of the available potential movements which can be made so as to best position the patient while avoiding significant movement of the patient out of the configuration set for the surgical procedure. In some cases some adjustment for the configuration is necessary in this movement within the bore but it will be appreciated that this is minimized in order to avoid compromising the surgical procedure. In some cases no movement of the configuration is possible in which case the movements allowed of the table are limited to those movements which maintain the configuration unchanged while optimizing the position of the part of the patient for imaging.

A system is provided to prevent damaging collisions between the patient and the table on one hand and the magnet on the other hand.

Control systems can be provided which calculate the position of the table and the patient prior to entry into the bore and during movement of the patient within the bore so as to avoid moving the patient to a position in which impact with the bore of the magnet may occur.

However for effective safety procedures it is also necessary to provide an impact detection system between the patient and the bore.

In one example this is provided using a laser system positioned within the bore which provides a series of beams within the bore which are broken in the event that the table or the patient approaches to close to the bore of the magnet. Such beams include directional arrangements together with receptors which receive the beams in their unbroken position and provide an indication if anyone of the beams is broken due to the movement of the patient or the table.

In a second example, an arrangement is provided which detects actual contact between an object and the inside surface of the bore. This construction may be of the type shown in U.S. Pat. No. 7,446,304 (Li) issued Nov. 4, 2008 to the present assignees, the disclosure of which is incorporated herein by reference. In this arrangement, therefore, the inside surface of the bore carries a flexible receiving surface which is deflected in the event of contact with an object within the bore so that the further movement of the patient and the table can be halted as soon as such a deflection is determined.

As a further alternative, a deflection system of this type can be provided on the table and/or on elements surrounding and identifying the location of the patient. Thus impact of the bore on the table itself or on one of these elements identifying the position of the patient triggers a signal in the element itself which again halts the movement of the patient and the table to the unsuitable position.

Figure 5:
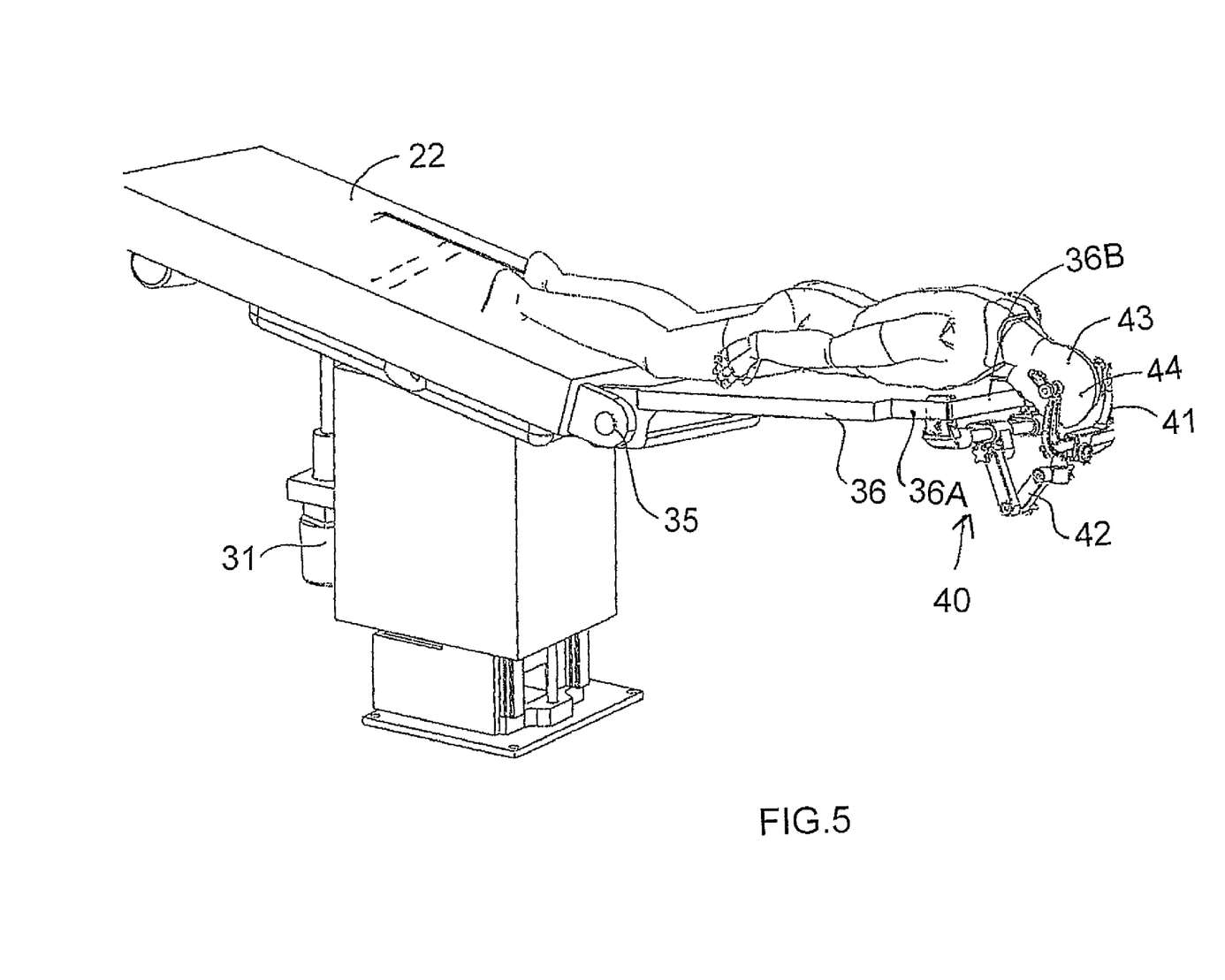
FIG. 5 is an isometric view of the table of FIG. 1 for mounting the patient showing a configuration for a head procedure.

Turning now to FIG. 5, there is shown an arrangement of the table which is established for procedures on the head of the patient. In this arrangement the patient is positioned on the table so that the legs of the patient are on the table member 22 with the knees of the patient at the hinge line 35. The portion 36 is then inclined upwardly and forwardly from the hinge line 35 so that the portion 22 and the portion 36 define a shallow obtuse angle. As shown the table portion 22 is inclined forwardly and downwardly. In this arrangement the table portion 36 includes a head mount 40 with a clamp 41 and a mounting bracket 42. The mounting bracket 42 is attached on the underside of the end of the portion 36 at a narrower section 36A. The bracket is located underneath the forward end of the portion 36 so that the clamp 41 is positioned forwardly and downwardly from the end 36B of the portion 36. In this way the patient is laid prone on the table with the head facing downwardly and forwardly thus exposing the rear 43 of the head 44 for suitable surgical procedure at the rear of the skull or the base of the skull.

The positioning of the head of the patient forwardly and downwardly allows the configuration of the patient to be suitably arranged so that the patient can enter the bore. Once within the bore, the position of the head of the patient can be adjusted forwardly, rearwardly, side to side together with up and down and tilt movement as previously described so as to position the part of the head to be imaged in the best position within the field of view within the magnet.

Figure 6:
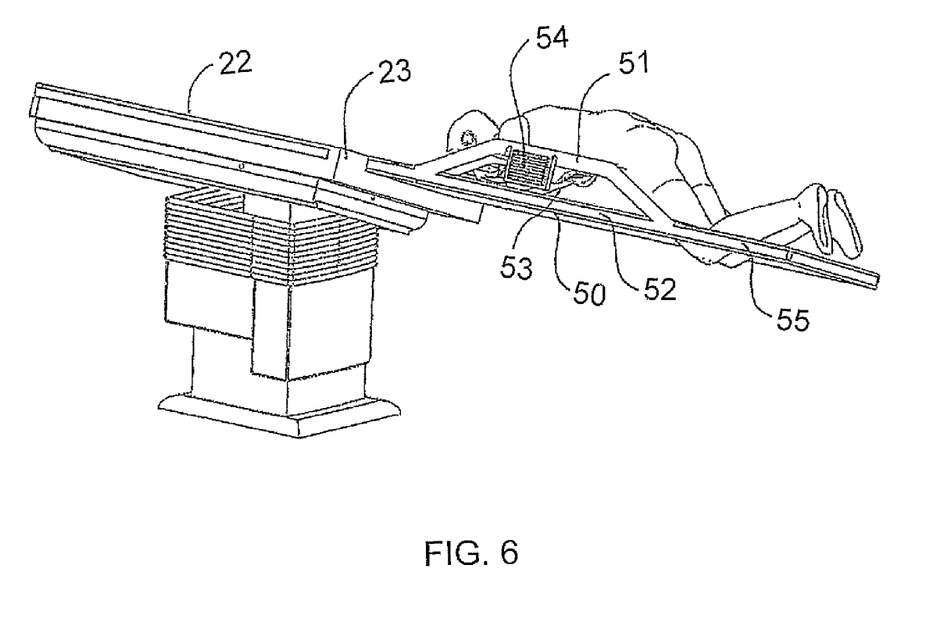
FIG. 6 is an isometric view of the table of FIG. 1 for mounting the patient showing a configuration for breast procedure.

In FIG. 6 is shown a construction provided for operations on the breast. In this arrangement, the table member 22 as a replacement table portion 50 attached at the receptacle 23. The table portion 50 has no transverse hinge line and is formed from a frame structure providing an arch section 51 over the base planar portion 52. The arch portion 51 has two sides located on respective sides of the patient together with transverse members which support the patient when laid in prone condition over the arch section 51 so that the breast area of the patient is located underneath the arch and above the planar base position 50 to allow access from open sides 53 of the structure. The arched frame 51 providing the openings 53 also allows for mounting of the RF coils 54. In this way the patient is supported prone with the knees projecting downwardly and rearwardly from the rear of the arch with a patient draped over the arch and the knees and feet carried on the planar portion 50 at an outwardly projecting section 55 of that planar portion. Again the position of the patient within the bore after insertion of the patient into the bore can be adjusted by tilting movement as required to move the part to be imaged to the required position. The patient remains in the configuration draped over the arch and can be held in that position by straps or other restraints allowing the table to be tilted to one side if required for proper positioning of the part to be imaged.

For breast procedures, the patient is positioned face down (prone) with an opening on the breast area. Cushions support the head and the rest of the body through the sternum with the legs and upper pelvic are being bent. The position allows full unilateral and bilateral access to the breasts.

The arrangement of FIG. 6 can also utilize the known Wilson frame available from OSI of Union City Calif., the details of which are known to persons skilled in the art.

Turning now to FIG. 7, there is shown the structure used in FIGS. 4 and 5 in which the same structure is used for operation typically on the spine or back of the patient. In this arrangement, therefore, the hinge line 35 is located around the waist area of the patient with the legs located on the table member 22 and the upper torso of the patient draped in prone condition over the portion 36. In this arrangement the head is positioned at a location spaced from the forward most end of the portion 36. The portion 36 is bent downwardly so as to provide an angle slightly greater than the 180° so that the back area of the patient is stretched over the hinge line 35 allowing effective access to the back and spine of the patient. Again the arrangement as shown allows the structure to be properly positioned with the patient remaining the configuration required into the bore and then for the movement of the table to adjust the patient to the required position for imaging without changing the configuration of the patient that has been set for the surgery.

Figure 8:
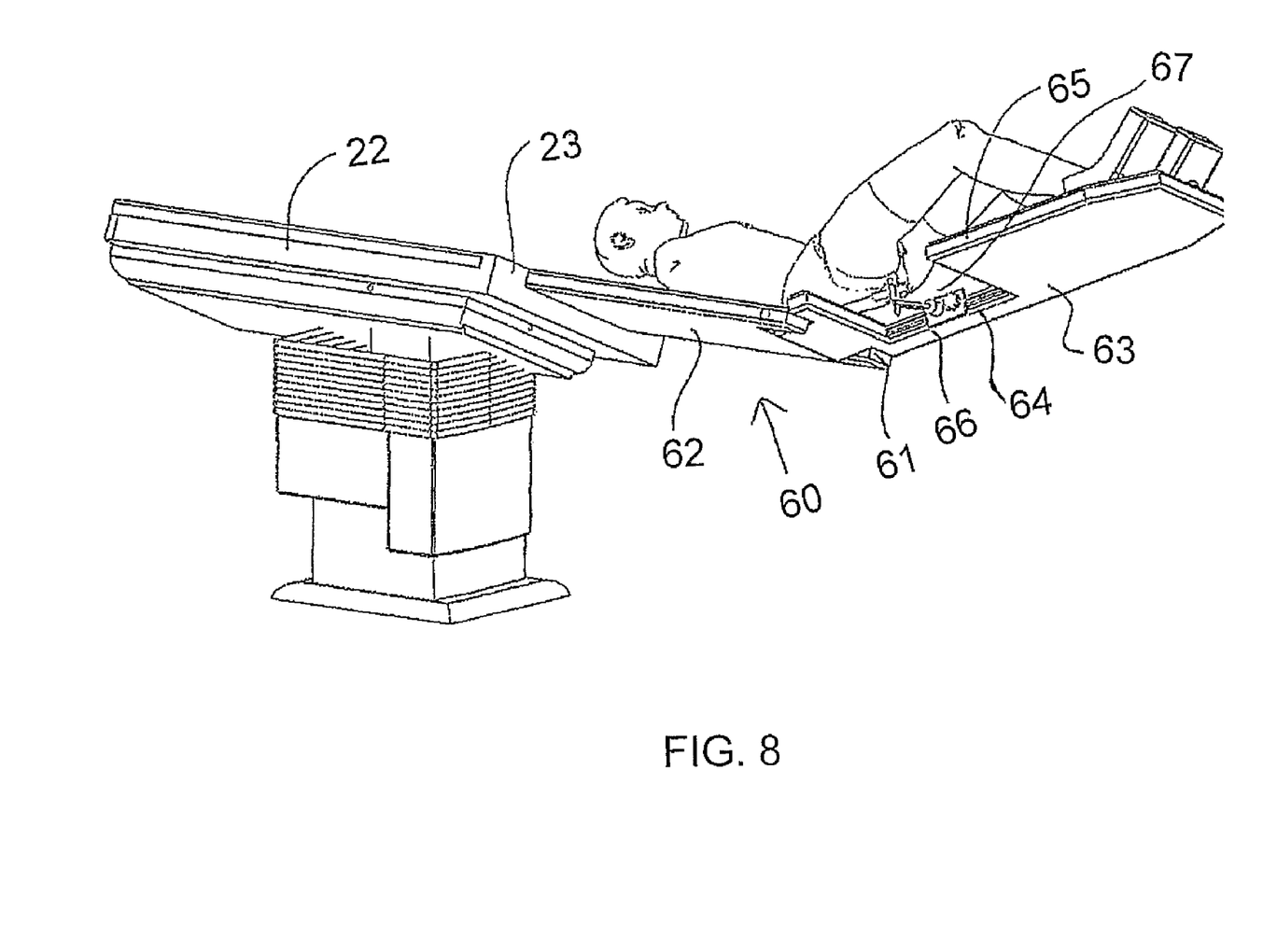
FIG. 8 is an isometric view of the table of FIG. 1 for mounting the patient showing a configuration for groin procedure.

Turning now to FIG. 8, there is shown a further arrangement of the table which utilizes a further table top portion 60 mounted on the table member 22 at the receptacle 23. In this arrangement the table top portion is designed for operation in the groin area for various procedures which are necessary at that location of the body. In this arrangement there is provided a hinge line 61 which is located at a position spaced from the table member 22 so as to provide a first portion 62 and a second portion 63 which can be arranged at an angle at the hinge line 61. An opening 64 is located in the second portion 63 just beyond the hinge line and extends from one side 65 to a narrow section 66 on the opposite side of the portion 63. This provides an opening 67 through which access can be made to the patient in the area required.

Turning again to FIGS. 1, 2 and 3 there is shown a system for use in radiation therapy of a lesion in a part of a patient. The patient support table described above is provided for receiving and supporting the patient during planning for and effecting of the therapy of the lesion. The patient support table is rotatable about the vertical axis to a first position 70 so as to co-operate with the magnetic resonance imaging system 3 for obtaining MR images of the lesion of the patient. The MRI system includes a magnet, at least one RF coil and an imaging control system 100.

The table can be moved to a second position 72 to co-operate with a CT imaging system 74 for generating a 360 degree scanned image of the patient at the location of the lesion, and to a third position 71 to co-operate with a radiation therapy system 75 for generating a beam of radiation for treatment of the lesion and for scanning the beam 360 degrees around the lesion. The CT system includes a control system 101.

Thus the magnetic resonance imaging system 3, the CT imaging system 74 and the radiation therapy system 75 are arranged at angularly spaced positions around the vertical axis of the pedestal of the patient support table.

The magnetic resonance imaging system is mounted so as to provide movement of the magnet relative to the table to enable the imaging of the patient while the patient remains in fixed position on the table.

The CT imaging system 74 is mounted on a movable mounting 77 to allow movement between the table and the CT system 74 to enable the imaging of the patient while the patient remains in fixed position on the table. Thus the CT system can be moved into imaging position when the magnet is retracted to the magnet bay and the CT system 74 can be retracted away when the CT imaging is complete.

Similarly the radiation therapy system is mounted on a movable mounting 78 so as to provide relative movement between the table and the radiation system to enable the radiation treatment of the patient when the magnet is retracted and while the patient remains in fixed position on the table. The radiation treatment includes a control 102 for receiving the input parameters defining the intended treatment pattern and for controlling the radiation accordingly.

Suitable mounting systems 77 and 78 for mounting and moving the CT system 74 and the Radiation system 75 are within the skill of a person skilled in this art so that no further detail will be provided here.

As shown in FIG. 2, an immobilization device 80 is provided for locating the part of the patient on the table so as to remain fixed relative to the table during the planning and therapy. When used for the head and neck area of the patient, the immobilization device 80 includes a head neck thermoplastic mask 81 which is molded to match the patient anatomy. Devices of this type are well known to a person skilled in the art. Further in FIG. 2, the immobilization device includes an immobilization board 82 arranged to be placed in fixed position on the table by fasteners 83. The RF coil 84 includes an anterior or top coil 85 and a posterior or base coil 86. The posterior coil is incorporated into the immobilization board in a manner which is capable of accepting the head neck thermoplastic mask fixed to the immobilization board at a fixed location, thus locating the area of the patient requiring treatment, in this case the head or neck area.

In some cases the table includes a perforated section 88 located underneath the location of the lesion and in the case of treatment to the head, the perforated section 88 is located at a perforated head extension board 89 of the table.

Arrangements of the above construction are shown in the above Publication 20090306495 Dec. 10, 2009, the disclosure of which is incorporated herein by reference.

The anterior coil portion 85 of the RF coil 84 is flexible so as to drape over the part of the patient. Such flexible structures formed from a suitable supporting fabric with the conductive coil contained within the fabric structures are generally known. The coil can also include a neck section 85A which drapes over the neck and upper chest of the patient which is a flexible or semi flexible neck piece that conforms to all the variety of neck sizes and extends up the lower torso area.

The head extension board and the immobilization board which lies upon it are formed of a fiber reinforced resin material where the fibers are non-conductive.

In use a central control system 103 is programmed to control the movement of the components and the operation of the imaging and treatment. This control 103 functions to cause the table to rotate around a vertical axis through the table so as to line up the table with the magnet, the CT scanning system and the radiation therapy system. The CT imaging system and the radiation therapy system are arranged so that the image and the treatment lie in a common plane around the lesion in the patient, with that plane being automatically arranged to overlie when the patient is moved between the two modalities by the fixed positioning of the patient relative to the table and the table relative to the two modalities. The treatment control system is arranged to locate the lesion using the MR image and to plan the radiation treatment to vary the intensity of radiation around the plane using the CT image. Thus registration between the MR image, the CT image and the radiation treatment is provided by the fixed position of the part of the patient on the table.

The table and the immobilization device including the board and the head/neck mask are MR compatible, radiation translucent, and non-conductive so as to allow the imaging and treatment of the patient while stationary on the table.

Typically, the immobilization board is made from Kevlar composite with conjunction of the urethane or Rohacell (trade mark) foams that is both radiolucent and MR compatible and has a cavity that incorporates the lower head portion of the head array coil that can be removable during radiation therapy procedure.

Suitable arrangements known to person skilled in the art can be used for the immobilization of the abdomen, pelvis, lower extremities, and upper extremities on the claims.

In FIG. 3 is shown an arrangement similar to FIG. 2 where the immobilization board 82 is omitted and instead the table is designed with the outer end arranged to receive the head and neck mask directly. In this arrangement, the table is also designed to receive the posterior coil 86A in a recess underneath the head support section.

Since various modifications can be made in my invention as herein above described, and many apparently widely different embodiments of same made within the spirit and scope of the claims without department from such spirit and scope, it is intended that all matter contained in the accompanying specification shall be interpreted as illustrative only and not in a limiting sense.

The invention claimed is:

1. A system for use in radiation therapy of a lesion in a part of a patient comprising:
    a patient support table for receiving and supporting the patient during planning for and effecting of the therapy of the lesion;
    an immobilization device for locating the part of the patient on the table so as to remain fixed relative to the table during the planning and therapy;
    a magnetic resonance imaging system for obtaining MR images of the lesion of the patient including a magnet, at least one RF coil and an imaging control system;
    a CT imaging system for generating a 360 degree scanned image of the patient at the location of the lesion;
    a radiation therapy system for generating a beam of radiation for treatment of the Lesion and for scanning the beam 360 degrees around the lesion;
    the magnetic resonance imaging system, CT imaging system and the radiation therapy system being arranged at angularly spaced positions around the patient support table
    the magnetic resonance imaging system being arranged so as to provide relative movement between the table and the system to enable the imaging of the patient while the patient remains in fixed position relative to the table;
    the CT imaging system being arranged so as to provide relative movement between the table and the system to enable the imaging of the patient while the patient remains in fixed position relative to the table;
    the radiation therapy system being arranged so as to provide relative movement between the table and the system to enable the radiation treatment of the patient while the patient remains in fixed position relative to the table;
    the CT imaging system and the radiation therapy system being arranged so that the image and the treatment being arranged such that they lie in a common plane around the lesion in the patient;
    the table and immobilization device being MR compatible, radiation translucent, and non-conductive so as to allow the imaging and treatment of the patient while stationary on the table;
    and a treatment control system arranged to locate the lesion using the MR image and to plan the radiation treatment to vary the intensity of radiation around the plane using the CT image.

2. The system according to claim 1 wherein the immobilization device includes a head neck thermoplastic mask which is molded to match the patient anatomy.

3. The system according to claim 1 wherein the immobilization device includes an immobilization board arranged to be placed in fixed position on the table.

4. The system according to claim 3 wherein where the RF coil includes a base part which is incorporated into the immobilization board which is capable of accepting the head neck thermoplastic mask.

5. The system according to claim 1 wherein the table includes a perforated section located underneath the location of the lesion.

6. The system according to claim 5 wherein the perforated section is located at a perforated head extension board.

7. The system according to claim 6 wherein head extension board is formed of a fiber reinforced resin material where the fibers are non-conductive.

8. The system according to claim 1 wherein the table rotates around a vertical axis through the table so as to locate the table in respective positions for cooperation with the magnet, the CT scanning system and the radiation therapy system.

9. The system according to claim 8 wherein the table is movable to the respective positions only by rotation around the axis.

10. The system according to claim 8 wherein the magnet is movable longitudinally so as to move into cooperation with the table.

11. The system according to claim 8 wherein the CT scanning system is movable relative to the table.

12. The system according to claim 8 wherein the radiation treatment system is movable relative to the table.

13. The system according to claim 1 wherein the RF coil includes an anterior coil which is flexible so as to drape over the part of the patient.

14. The system according to claim 1 wherein registration between the MR image, the CT image and the radiation treatment is provided by the fixed position of the part of the patient on the table.

15. The system according to claim 1 wherein the RF coil includes a flexible or semi flexible neck piece that conforms to all the variety of neck sizes and extends up the lower torso area.

16. The system according to claim 1 wherein the immobilization board is made from Kevlar composite with foams that is both radiolucent and MR compatible and has a cavity that incorporates the lower head portion of the head array coil that can be removable during radiation therapy procedure.

* * * * *